(12) United States Patent
Rey-Bayle et al.

(10) Patent No.: US 11,788,954 B2
(45) Date of Patent: Oct. 17, 2023

(54) METHOD FOR DETERMINING AT LEAST ONE PARAMETER THAT REPRESENTS A CHANGE IN A FLUID BY MULTI-POINT NEAR-INFRARED SPECTROSCOPY

(71) Applicant: IFP Energies nouvelles, Rueil-Malmaison (FR)

(72) Inventors: Maud Rey-Bayle, Rueil-Malmaison (FR); Noemie Caillol, Rueil-Malmaison (FR); Cyril Cassar, Rueil-Malmaison (FR); Myriam Darbouret, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 79 days.

(21) Appl. No.: 17/293,376

(22) PCT Filed: Oct. 30, 2019

(86) PCT No.: PCT/EP2019/079625
§ 371 (c)(1),
(2) Date: May 12, 2021

(87) PCT Pub. No.: WO2020/099130
PCT Pub. Date: May 22, 2020

(65) Prior Publication Data
US 2022/0003666 A1    Jan. 6, 2022

(30) Foreign Application Priority Data

Nov. 16, 2018 (FR) ........................... 1871571

(51) Int. Cl.
*G01N 21/3577* (2014.01)
*G01N 21/359* (2014.01)
*G01N 33/28* (2006.01)

(52) U.S. Cl.
CPC ....... *G01N 21/3577* (2013.01); *G01N 21/359* (2013.01); *G01N 33/2823* (2013.01)

(58) Field of Classification Search
CPC ............. G01N 21/3577; G01N 21/359; G01N 33/2823; G01N 33/2811; G01N 21/51; G01N 33/2835
See application file for complete search history.

(56) References Cited

U.S. PATENT DOCUMENTS 5,454,257 A     10/1995  Fotland et al.
6,841,779 B1 *  1/2005   Roehner ............ G01N 33/2811
                                                  250/339.06
(Continued)

FOREIGN PATENT DOCUMENTS

FR        2647903 A1      12/1990
WO    2016/209248 A1      12/2016

OTHER PUBLICATIONS

Rey-Bayle et al., Apr. 1, 2019, Multiangle near infrared spectroscopy associated with common components and specific weights analysis for in line monitoring, Journal of Near Infrared Spectroscopy, vol. 27, pp. 134-146. (Year: 2019).*

(Continued)

*Primary Examiner* — Christine S. Kim
(74) *Attorney, Agent, or Firm* — Fitch, Even, Tabin & Flannery LLP

(57) ABSTRACT

The invention is a method of determining at least one parameter representative of a change in a fluid due to a temperature variation of the fluid. The method includes placing the fluid in a medium transparent to radiation in a near-infrared domain; b) performing a spectral measurement by use of spatially resolved near-infrared spectroscopy for the fluid placed in the transparent medium, the spectral measurement being performed for at least two measurement angles and for at least two temperatures of the fluid; c)

(Continued)

performing a multivariate analysis of the spectral measurement as a function of the temperature; and d) determining the parameter representative of a change in the fluid by using the multivariate analysis.

22 Claims, 6 Drawing Sheets

(56) References Cited

U.S. PATENT DOCUMENTS

| | | | |
|---|---|---|---|
| 8,326,548 B2 * | 12/2012 | Oh | G01N 21/3577 |
| | | | 250/339.06 |
| 2007/0143023 A1 * | 6/2007 | Betancourt | G01N 1/00 |
| | | | 702/11 |
| 2016/0097717 A1 | 4/2016 | Yuen et al. | |
| 2016/0208601 A1 | 7/2016 | Molla et al. | |
| 2017/0363540 A1 * | 12/2017 | Koseoglu | G01N 21/359 |
| 2019/0128117 A1 * | 5/2019 | Dumont | E21B 49/10 |

OTHER PUBLICATIONS

Paso et al., Measurement of Wax Appearance Temperature Using Near-Infrared (NIR) Scattering, 2009, Energy Fuels, vol. 23, pp. 4988-4994, (Year: 2009).*
International Search Report for PCT/EP2019/079625, dated Feb. 12, 2020.

* cited by examiner

[Fig 1]
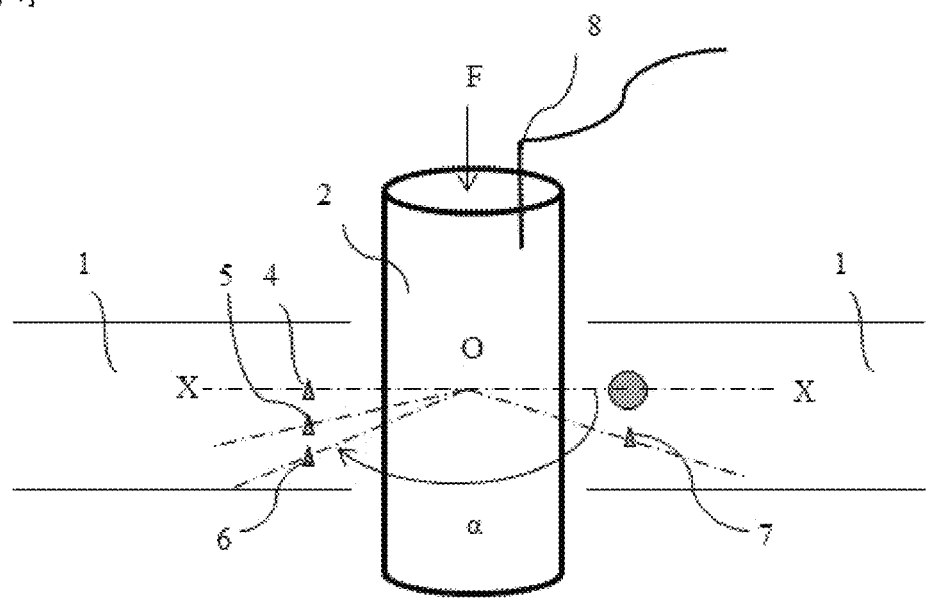

[Fig 2]
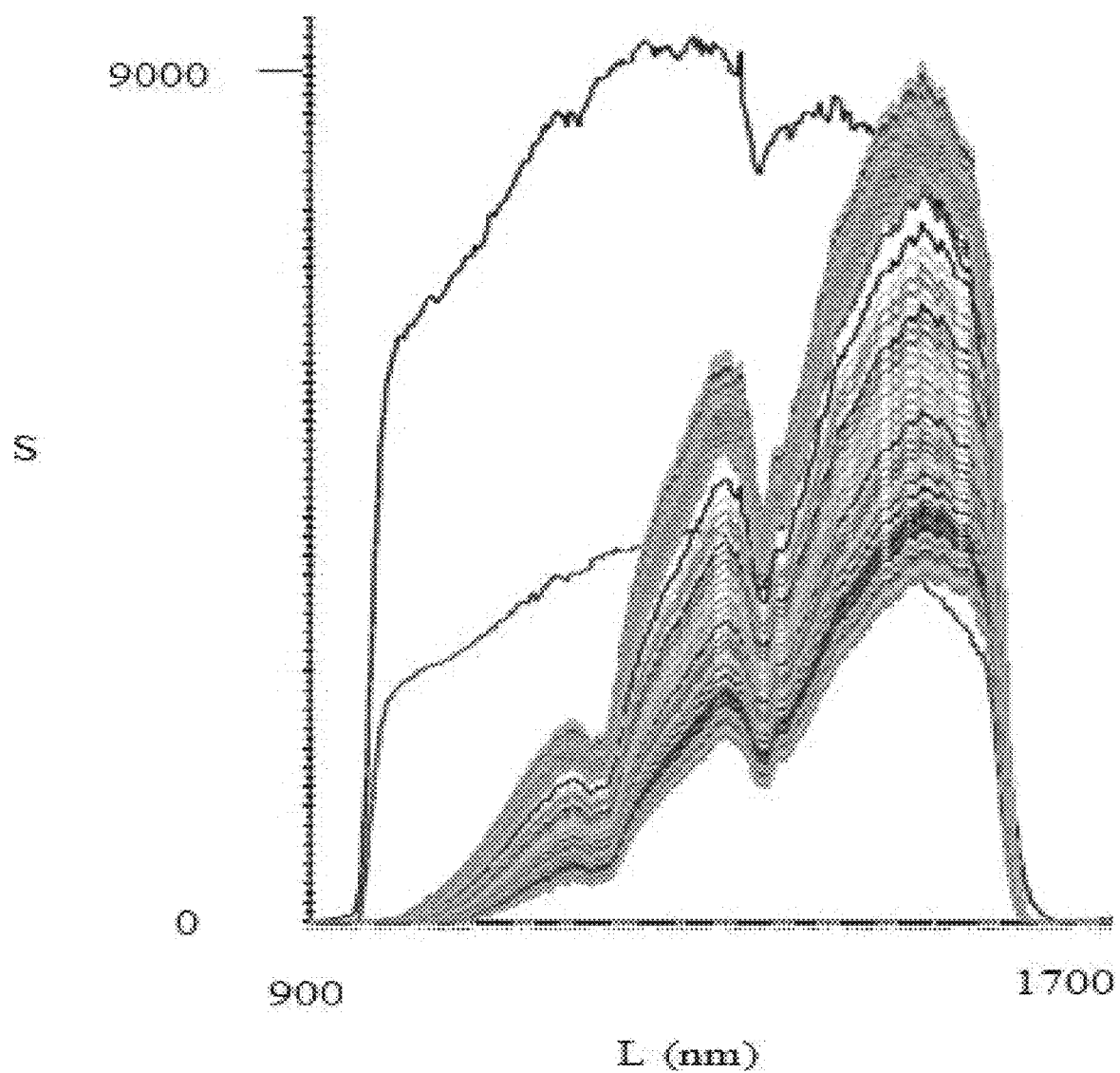

[Fig. 3]
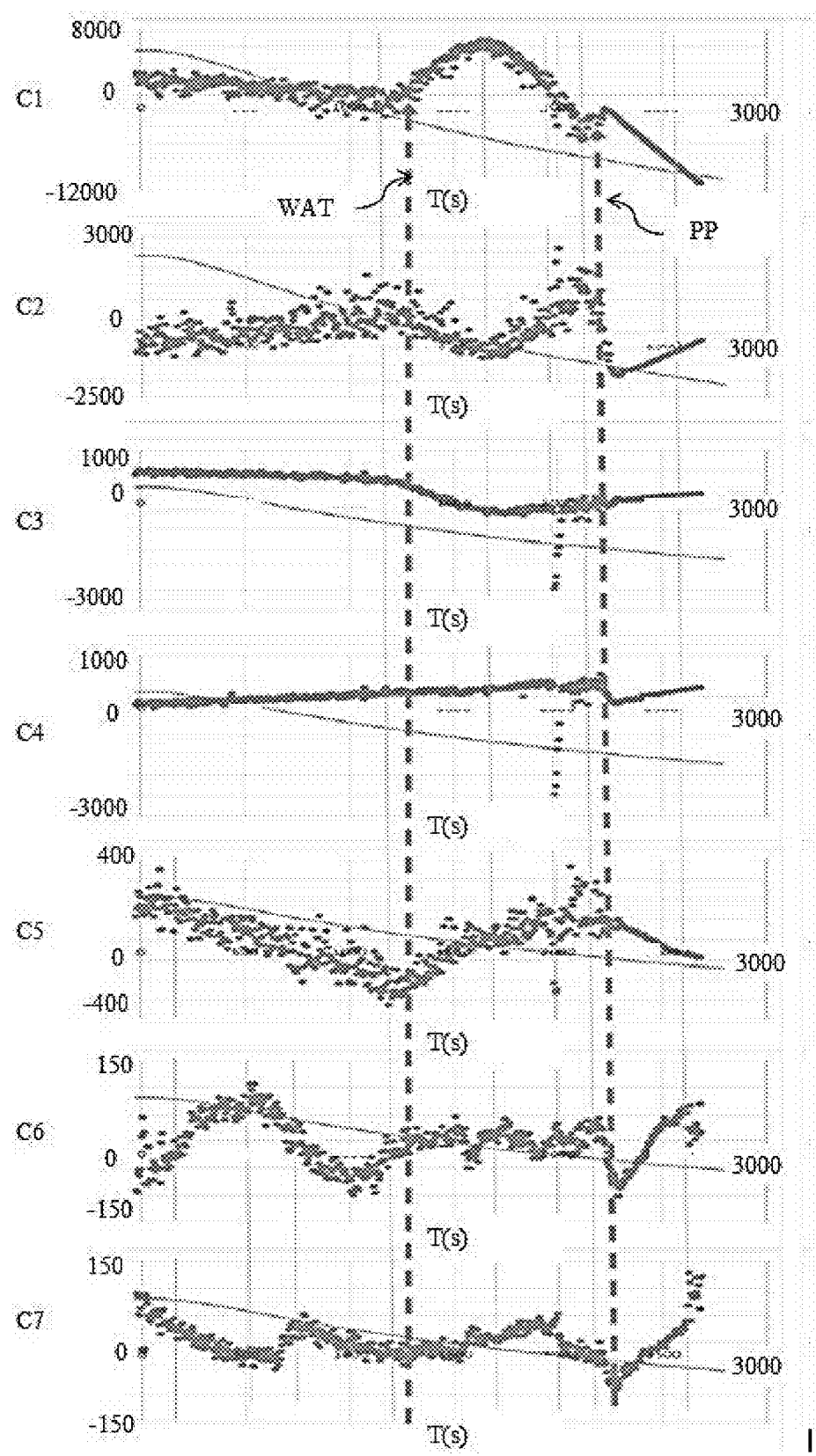

[Fig 4]
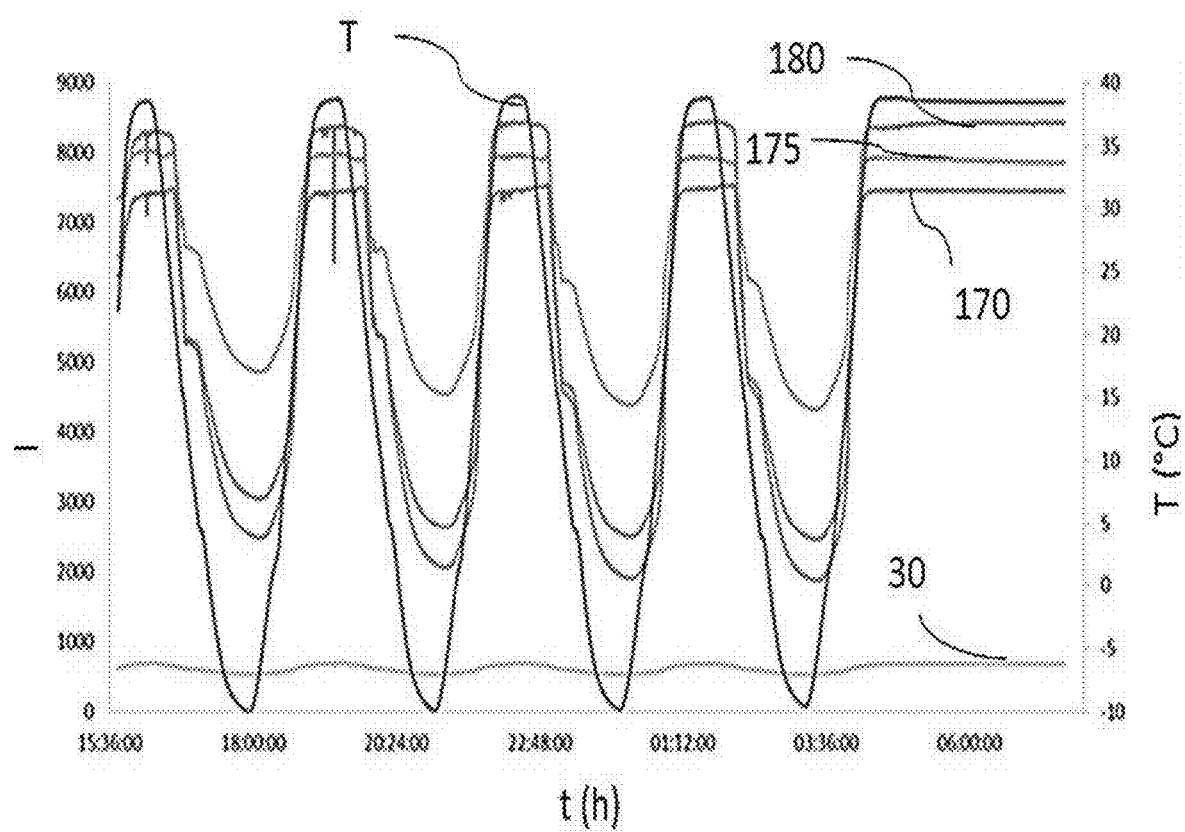

[Fig 5]
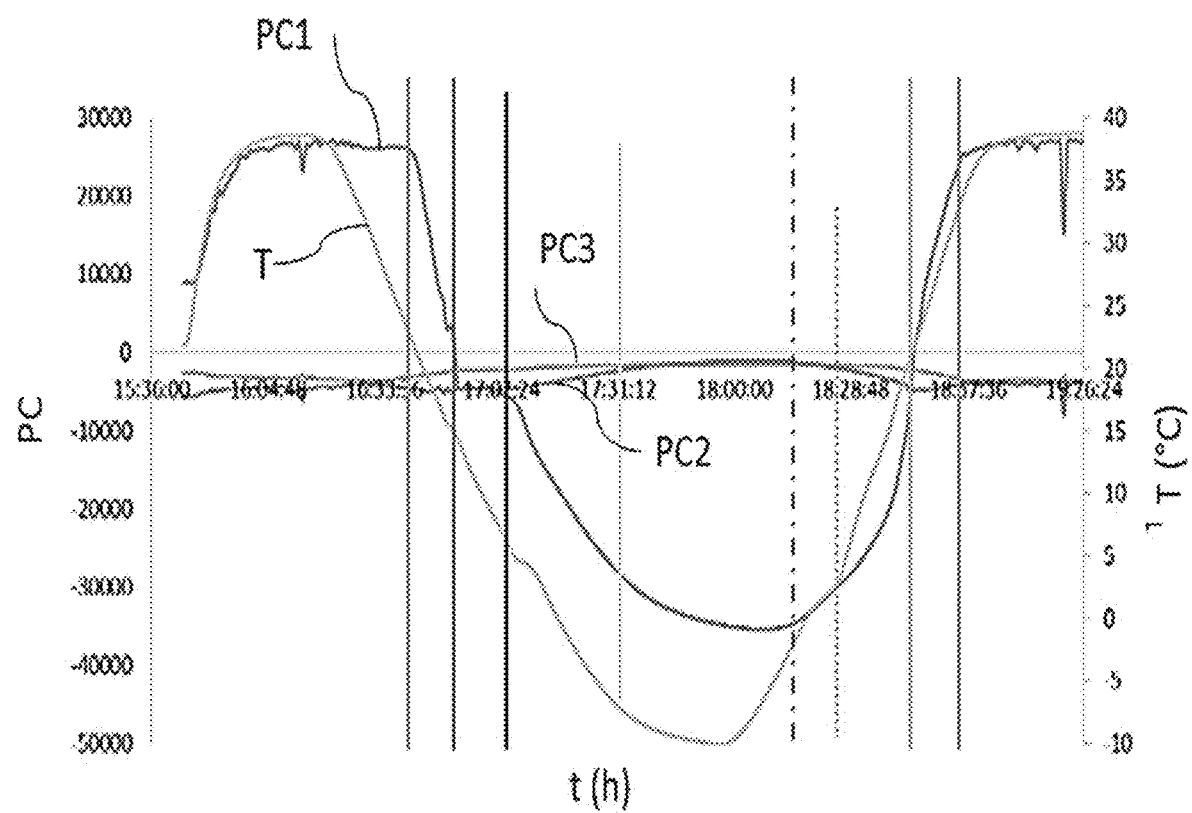

[Fig 6]
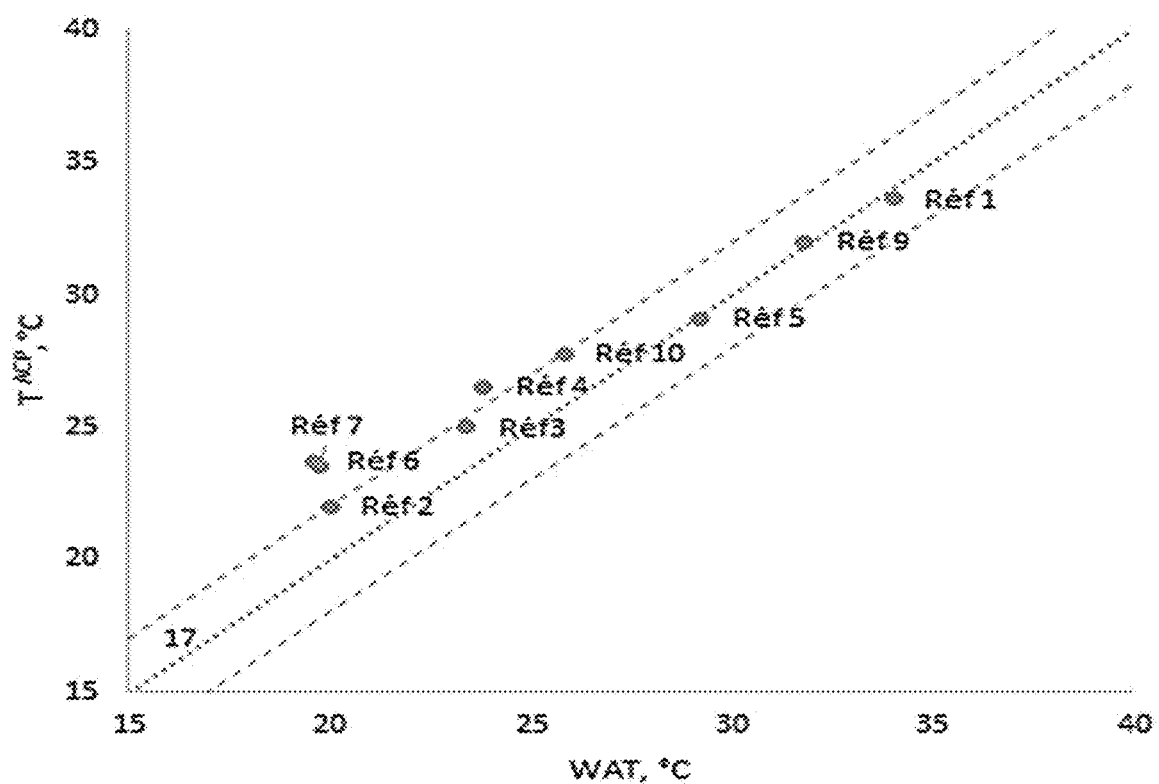

METHOD FOR DETERMINING AT LEAST ONE PARAMETER THAT REPRESENTS A CHANGE IN A FLUID BY MULTI-POINT NEAR-INFRARED SPECTROSCOPY

CROSS-REFERENCE TO RELATED APPLICATIONS

Reference is made to PCT/EP2019/079625 filed Oct. 30, 2019, and French Patent Application No. 1871571 filed Nov. 16, 2018, which are incorporated herein by reference in their entirety.

BACKGROUND OF THE INVENTION

Field of the Invention

The present invention relates to the field of fluid characterization, in particular to a crude oil. Characterization of the fluid determines at least one parameter of the fluid, the parameter being related to a change (i.e. a transition) in the fluid due to a fluid temperature variation. In particular, the invention relates to at least one of the determination of the wax appearance temperature WAT in the fluid and of the pour point PP of the fluid.

The invention is notably suitable for characterizing and understanding the cold properties of petroleum products for refining and in the field of exploration-production.

Cold properties are characterized, among other things, by the wax appearance temperature WAT and the pour point PP. Conventionally, characterization of these two properties is normalized by differential scanning calorimetry DSC for the WAT and by a physical measurement via inclination of a vessel at different temperatures for the PP. These methods are long, have proved inaccurate and cannot be implemented online for the flow conditions of the petroleum products. Indirect approaches have been developed but they only enable partial access to the cold behavior of the products. Besides, most commercial solutions are not suitable for opaque or black products such as crude oils.

Determination of cold properties in the oil sector is not a new research topic. Many methods have already been developed.

A first solution, described in U.S. Pat. No. 5,454,257, determines wax appearance from the change in volume of the cell containing the petroleum product as a function of temperature. Such a method requires a fluid sample and it cannot be used online on a continuous basis.

Another method, notably described in U.S. published patent application 2016/0208601, relates to WAT determination by determining the temperature at which the pressure is no longer stable in a microfluidic system where the product flows. Such a method also requires a fluid sample and it cannot be used for online monitoring of a continuous fluid circulation.

There are also solutions using measurements in the medium to determine cold properties, based on the interactions of light with matter. Several studies use near-infrared transflectance spectroscopy. The document "Paso K, Kallevik H, Sjöblom J. Measurement of Wax Appearance Temperature Using Near-Infrared (NIR) Scattering. Energy Fuels 2009; doi:10.1021/ef900173b" describes WAT determination on several petroleum fluids (crude oils, waxy gas condensate, and samples of macrocrystalline and microcrystalline paraffin wax in dodecane). The authors follow at a few wavelengths the optical density of the scattered light. No multivariate analysis of the spectral measurements has been carried out to precisely determine the WAT.

The document "Santos D, Filho E B M, Dourado R S, Amaral M, Filipakis S, Oliveira, Lize M. S. L., Guimarães R C L, Santos A F, Borges G R, Franceschi E, Dariva C. Study of Asphaltene Precipitation in Crude Oils at Desalter Conditions by Near-Infrared Spectroscopy. Energy Fuels 2017; doi:10.1021/acs.energyfuels.7b00602" illustrates the determination of the precipitation of asphaltenes in a crude by a measurement at a single point.

Another invention, as described notably in U.S. published patent application 2003/0075478, also determines the WAT online by use of the reflection of a laser source.

Furthermore, another method, notably described in U.S. published patent application 2016/0097717, relates to a system enabling to determine the wax appearance and disappearance temperature in transparent, translucent and opaque oils by measuring the scattered signal at a reflection point. The system allows circulation and heating of the fluid. Such a method requires a fluid sample and it cannot be used for online monitoring of a continuous fluid circulation.

Furthermore, it is also interesting to determine other parameters representative of changes in a fluid. It can notably be parameters related to a transition threshold between the phases of the fluid, a cloud point, a parameter related to an aggregation or agglomeration of objects within the fluid, such as, for example the generation of nano-aggregates.

SUMMARY OF THE INVENTION

To overcome these drawbacks, the present invention relates to a method of determining at least one parameter representative of a change in a fluid due to a temperature variation of the fluid, wherein the fluid is placed in a medium transparent to the near-infrared domain and a spectral measurement is performed by multipoint and multi-temperature near-infrared spectroscopy (also referred to as spatially resolved near-infrared spectroscopy). The desired parameter is then deduced by multivariate analysis of the measurement. The method according to the invention is suited to any type of fluid, including opaque fluids, by use of spatially resolved spectroscopy, and allows to performance rapidly and simply of online measurements for monitoring a continuous circulation of a fluid by means of near-infrared spectroscopy. Furthermore, multipoint and multi-temperature spectroscopy allows accurate obtaining of the desired parameter and, if necessary, determination of several parameters of the fluid. Indeed, multivariate analysis allows several fluid characteristics to be determined.

Moreover, the invention relates to a method for at least one of monitoring and controlling a fluid flow in a pipe by implementing such a method of determining a parameter representative of a change in the fluid.

The present invention relates to a method of determining at least one parameter representative of a change in a fluid due to a temperature variation of the fluid. The method comprises the following steps:

a) placing the fluid in a medium transparent to radiation in a near-infrared domain;

b) performing a spectral measurement by spatially resolved near-infrared spectroscopy for the fluid placed in the transparent medium, the spectral measurement being performed for at least two measurement angles and for at least two temperatures of the fluid;

c) performing a multivariate analysis of the spectral measurement as a function of the temperature; and d) determining the parameter representative of a change in the fluid by use of the multivariate analysis.

According to one embodiment, the parameter representative of a change in the fluid is selected from among the wax appearance temperature of the fluid, the pour point of the fluid, a cloud point, a cold filter plugging point, a transition threshold between the phases of the fluid, a parameter related to aggregation or agglomeration of objects within the fluid, such as the generation of nano-aggregates, the growth of objects, the polydispersity of objects.

Preferably the parameter representative of a change in the fluid is the wax appearance temperature of at least one of fluid and the pour point of the fluid.

Advantageously, the fluid is a crude oil.

According to an aspect, the fluid is placed in a bypass line of a pipe through which the fluid flows.

According to an embodiment, the spatially resolved near-infrared spectroscopy is performed by use of at least one transmission measurement, notably with a measurement angle (a) ranging between 130° and 180°, preferably between 165° and 180°.

Advantageously, the spatially resolved near-infrared spectroscopy is performed by use of at least one reflection measurement, notably with a measurement angle (a) ranging between 5° and 90° and preferably between 20° and 40°.

Advantageously, the spatially resolved near-infrared spectroscopy is performed by use of at least two transmission measurements with respectively measurement angles (a) selected from about 170°, 175° and 180°, and at least one reflection measurement with a measurement angle (a) of about 30°.

According to a feature, the multivariate analysis is a principal component analysis or a common component and specific weight analysis.

Preferably, the multivariate analysis is performed for at least six components.

Advantageously, the parameter representative of a change in the fluid is determined by analysis of at least one of inflection point, and a break of slope and the limitation from the noise of at least one component of the multivariate analysis.

According to an embodiment, the spatially resolved near-infrared spectroscopy is carried out with a wavelength variation between a minimum value ranging between 780 nm and 1000 nm, and a maximum value ranging between 1700 nm and 2500 nm, preferably the wavelength variation ranges between 900 nm and 1700 nm.

According to an implementation, the temperature of the fluid placed in the transparent medium is controlled for carrying out the spectral measurement, preferably by varying the temperature of the fluid between a minimum temperature ranging between −20° C. and 15° C. and a maximum temperature ranging between 30° C. and 60° C.

According to an embodiment, the fluid is circulated in a pipe and the spectral measurement is performed in a bypass line of the pipe through which the fluid flows.

According to an aspect, during the spectral measurement, circulation of the fluid in the bypass line is stopped.

Furthermore, the invention relates to a at least one of method of monitoring and controlling the flow of a fluid through a pipe. The following steps are carried out for this method:
  a) determining at least one parameter representative of a change in the fluid within the pipe due to a temperature variation of the fluid by using the method according to one of the above features; and
  b) at least one of monitoring and controlling the flow of the fluid through the pipe according to the parameter representative of a change in the determined fluid.

BRIEF DESCRIPTION OF DRAWINGS

Other features and advantages of the method according to the invention will be clear from reading the description hereafter of embodiments given by way of non-limitative examples, with reference to the accompanying figures wherein:

FIG. 1 illustrates an SRS probe and a tube for implementing the method according to an embodiment of the invention;

FIG. 2 illustrates a set of SRS spectral measurements for a sample during a temperature cooling cycle for an example according to the invention;

FIG. 3 shows the curves of a multivariate analysis for an example according to an embodiment of the example;

FIG. 4 shows the follow-up of a mixture of crude oils at a wavelength for the 4 detection angles during 5 successive temperature cycles for an example according to an embodiment of the invention;

FIG. 5 shows the scores during a cycle of the first three principal components calculated based on comprehensive data for an example according to an embodiment of the invention; and FIG. 6 shows the WAT obtained by analysis of the PCA scores as a function of the WAT obtained with the reference method for an example according to an embodiment of the invention.

DETAILED DESCRIPTION OF THE INVENTION

The present invention relates to a method of determining in real time at least one parameter of a fluid. The parameter is representative of a change such as a transition or a variation in the fluid related to a temperature variation of the fluid. Such a parameter is also referred to as cold property of the fluid.

Advantageously, the parameter representative of a change in the fluid can be selected from among the wax appearance temperature WAT of the fluid, the pour point PP of the fluid, the cloud point, the cold filter plugging point, a transition threshold between the phases of the fluid, a parameter related to an aggregation or an agglomeration of objects within the fluid, such as the generation of nano-aggregates, the growth of objects, the polydispersity of objects, the precipitation of asphaltenes, the crystallization of water to hydrate, the wax disappearance temperature.

Preferably, the parameter representative of a change in the fluid can be at least one of the wax appearance temperature WAT of the fluid and the pour point PP of the fluid. Preferably, the method according to the invention can determine the WAT and the PP.

The fluid can be of any type, in particular an organic fluid, for example a fluid of petroleum origin, preferably a petroleum fluid, more preferably a crude oil, a paraffinic crude for example. Indeed, the method according to the invention is suitable for any type of fluid and it operates for opaque fluids as well as clear fluids (transparent, translucent) or cloudy fluids. Alternatively, the fluid can be kerosene or a distillate.

The method according to the invention is particularly well-suited to determining the wax appearance temperature WAT and the pour point PP of a crude oil.

For the embodiment where the fluid is kerosene, the parameter representative of a change in the fluid can be the freezing point. For the embodiment where the fluid is a distillate, the parameter can be at least one of the pour point, the cold filter plugging point CFPP, and the cloud point CP.

For the method according to the invention, the following steps are carried out:
a) placing a fluid in a medium transparent to the near-infrared domain;
b) performing a spectral measurement by spatially resolved near-infrared spectroscopy (NIR-SRS) for the fluid placed in the transparent medium, the spectral measurement being performed for at least two measurement angles and for at least two temperatures of the fluid placed in the transparent medium;
c) performing a multivariate analysis of the spectral measurement as a function of temperature; and
d) determining the parameter representative of the change in the fluid by using the multivariate analysis.

Multipoint NIR-SRS spectroscopy measures the signal at different points from a light source that emits in the near-infrared domain such as with wavelengths ranging between 0.78 μm and 3 μm. The spectra obtained can be measured in reflection mode or in a configuration allowing signal acquisition in reflection and transmission mode. The SRS measurements associated with multivariate analysis tools (also referred to as chemometric tools) highlight the various phenomena present in the monitored medium.

Near-Infrared Spectroscopy (NIRS) involves many advantages for monitoring processes. Beyond practical aspects, one of the main reasons for using it is its ability to rapidly and simply provide physical and chemical information. However, in the case of at least one of heterogeneous and complex media, measuring the signal at a single point may be insufficient. One solution measures the medium at several points and in applying multivariate analysis tools. The method according to the invention allows performing rapid and simple online measurements for monitoring a continuous circulation of a fluid by use of near-infrared spectroscopy.

Spectral measurement on a flowing fluid enables continuous and real-time monitoring of the parameter representative of the change in the fluid. Furthermore, performing the measurement for plural fluid temperatures allows accurate analysis of the change in the fluid as a function of temperature.

For the method according to the invention, an SRS Sam-Flex™ probe (Indatech-Chauvin Arnoux, France) can be used.

According to an aspect of the invention, the medium transparent to the near-infrared domain can be a transparent tube. A quartz tube can be used as the tube transparent to the near-infrared domain. This material is suitable for NIR-SRS measurements.

According to an embodiment of the invention, the fluid is circulated in a bypass line of a pipe carrying the fluid. In other words, the measurement is performed in a branch parallel to a pipe through which the fluid flows. It is thus possible to monitor the evolution of the fluid, notably as a function of temperature, within a pipe, in real time and continuously during a temperature cycle, without slowing or stopping the main flow, via a continuously fed fast loop where the flow would be stopped for the duration of a temperature analysis cycle. For example, the method according to the invention allows carrying out a "stop flow" analysis in a bypass line of a pipe in which the fluid flows. In other words, a pipe carrying the fluid to be analyzed comprises a bypass line in which the fluid also circulates, and the measurement is performed by near-infrared spectroscopy in this bypass line. To perform the measurement, circulation of the fluid is stopped in the bypass line only. Once the measurement is performed, the fluid is again allowed to circulate in the bypass line and the measurement can be repeated if need be. Thus, the fluid flow in the pipe is not perturbed and this method does not require taking a sample of the fluid.

In order to obtain accurate measurements, the NIR-SRS spectroscopy can be carried out by plural measurements (in other words, with a plurality of measurement points), with at least two measurement angles. A measurement angle is understood to be the angle formed between the direction of the signal from the light source and the direction in which the sensor receives the signal. The method is referred to as multipoint spectroscopy when measurements are used.

According to an embodiment of the invention, NIR-SRS spectroscopy can be performed by using at least one transmission measurement. The transmission measurement can be performed with a measurement angle ranging between 90° and 180° with respect to the source, preferably between 165° and 180°, for example with values such as 170°, 175° or 180°. Between 175° and 180°, NIR-SRS spectroscopy is more sensitive to the scattering variations linked with small particles.

In addition to transmission measurement, NIR-SRS spectroscopy can be performed by at least one reflection measurement, also referred to as backscatter. Reflection measurement can be carried out with a measurement angle ranging between 5° and 90°, preferably between 20° and 40°, as for example with a value of 30°.

According to a first example embodiment of the invention, NIR-SRS spectroscopy can be performed by at least two transmission measurements, with respectively measurement angles of about 175° and about 180°, and by using of at least one reflection measurement with a measurement angle of about 30°. The interest of this multipoint measurement configuration is to have both reflection measurements and transmission measurements to enable spectral measurement and therefore accurate multivariate analysis.

According to a second example embodiment of the invention, NIR-SRS spectroscopy can be performed by three transmission measurements, with respectively measurement angles of about 170°, about 175° and about 180°, and by a reflection measurement with a measurement angle of about 30°. The interest of this multipoint measurement configuration is to have both reflection measurements and transmission measurements to enable spectral measurement and therefore accurate multivariate analysis. The addition of one transmission measurement point in relation to the first example embodiment makes it possible to have some more information on the various sizes of the fluid particles that scatter light.

According to an aspect of the invention, spatially resolved near-infrared spectroscopy can be implemented for a wavelength of the scattering source ranging from a minimum value between 780 nm and 1000 nm to a maximum value between 1700 nm and 3000 nm, preferably with the wavelength variation ranging between 900 nm and 2200 nm. Thus, the method according to the invention covers a wide range of wavelengths, which allows obtaining parameters related to a change in the fluid, such as parameters related to the precipitation of asphaltenes or the parameters related to the SARA (Saturate Aromatic Resin and Asphaltene) composition of the fluid. Moreover, in order to improve the small object detection sensitivity, it is preferable to have a wavelength variation comprising small values (800 nm for example).

FIG. 1 schematically illustrates, by way of non-limitative example, a NIR-SRS probe 1 and a tube 2 for implementing the method according to an embodiment of the invention. A fluid F is positioned within tube 2 (the direction of flow of the fluid does not matter). A light source 3 with a direction of illumination XX is placed in the NIR-SRS probe. Furthermore, the NIR-SRS probe comprises four light sensors 4, 5, 6 and 7. Light sensors 4, 5, 6 and 7 can be offset: the probe can comprise optical fibers (not shown) for transmitting optical signals to light sensors 4, 5, 6 and 7. The sensors arranged opposite light source 3 are sensors for transmission measurements and the sensors arranged on the same side as the light source are reflection measurement sensors. These four light sensors are arranged as follows: three in transmission 4, 5 and 6, and one in reflection 7. In this figure, the direction of the light signals is shown by discontinuous lines. The measurement angles correspond to the angles formed by the line segment between light source 3 and point O, with the line segment formed by point O and sensor 4, 5, 6 or 7. For example, angle α represents the measurement angle of sensor 6. Sensor 4 (transmission referred to as collimated transmission) is on axis XX, with a measurement angle of 180°. Sensor 5 (transmission referred to as diffuse transmission) is slightly offset with respect to sensor 4 and it has a measurement angle of 175°. Sensor 6 (transmission referred to as diffuse transmission) is slightly offset with respect to sensor 5 and it has a measurement angle of 170°. Sensor 7 (reflection also referred to as backscatter) is offset with respect to axis XX, with a measurement angle of 30°.

Furthermore, the measurement system can optionally comprise a temperature sensor 8 for measuring the temperature in tube 2.

In addition, according to an implementation of the invention, the measurement system can also include a regulation system (not shown) for the temperature of tube 2 in order to control the temperature of fluid F, for example by decreasing the temperature of fluid F.

The spectra processing step by multivariate analysis of data obtained through NIR-SRS spectroscopy makes possible differentiation of the information contained in the spectra. Various methods can therefore be implemented, such as a principal component analysis (PCA) or a common component and specific weight analysis (CCSWA). These methods provide fast differentiation. It is thus possible to determine the parameter representative of a change in the fluid on a continuous basis. Besides, multivariate analysis allows determination by using measurements with a single device (spatially resolved near-infrared spectroscopy) with plural parameters being representative of a change in the fluid. For example, the method according to the invention allows determination with a single measurement the wax appearance temperature and the pour point of the fluid.

PCA is a multivariate data analysis tool allowing exploration of a data set with a large number of variables. PCA represents the individuals (samples) in a more reduced space defined by the variables. It is a method that has the goal of finding the directions of greater dispersion of the individuals in this space. The benefit is that the directions of greater dispersion are the most interesting directions. If the variables contain only noise, the individuals are homogeneously and uniformly dispersed in all directions. A direction that deviates from such a spherical distribution can potentially contain information. Mathematically, PCA calculates linear combinations of the original variables generating new axes, referred to as principal components (PC), which contain the major part of the variability of the original data matrix. It simply assumes that the directions of greater dispersion of the samples are the most interesting directions and that the variability associated with these directions corresponds to information. Furthermore, to avoid having the same "information" in several Principal Components all components need to be orthogonal. Matrix decomposition of the PCA allows obtaining score matrices and loading matrices.

CCSWA is a multivariate analysis tool enabling simultaneous analysis of data matrices, considered as tables, and extraction of the common information among them. Initially, this method was developed by Qannari et al. (described for example in the document Hanafi M., Qannari E M. Nouvelles propriétés de l'analyse en composantes communes et poids spécifiques. Journal de la Société Française de Statistique 2008; 149(2)) for analyzing data from sensory studies. More recently, it was used for studying samples measured with various devices in order to find correlations between data tables and to discriminate samples using the global information contained in each table.

According to an implementation of the invention, for a multivariate PCA or CCSWA type analysis, at least six components can be determined for obtaining precise information and enabling obtaining plural parameters related to a change in the fluid.

According to an embodiment of the invention, the parameter representative of a change in the fluid can be determined by analysis of at least one of an inflection point, a break of slope and the limitation of the noise of the signal from at least one component of the multivariate analysis. Indeed, the at least one inflection points, breaks of slope, and the presence of noise of the components of the multivariate analysis indicate variations or changes in the fluid.

According to an implementation of the invention, the temperature of the fluid circulating in the transparent medium can be controlled to carry out the spectral measurement. For this implementation, the temperature of the fluid can be varied between a minimum temperature ranging between −20° C. and 15° C. and a maximum temperature ranging between 30° C. and 60° C. It is thus possible to accurately analyze the change(s) in the fluid and to obtain the desired parameter.

According to an aspect of the invention, the method can also comprise a step of measuring the temperature of the fluid in the transparent medium. This temperature measurement step can be carried out by using a temperature probe in the transparent medium.

Furthermore, the present invention relates to a method of at least one monitoring and controlling the flow of a fluid (crude oil for example) in a pipe. In this case, the following steps are carried out:

a) determining at least one parameter representative of a change in the fluid within the pipe due to a temperature variation of the fluid by using the method according to any one of the above variants; and b) at least one of monitoring and controlling the fluid flow in the pipe according to the parameter representative of a change in the fluid determined in the previous step.

According to an embodiment of the invention, within the context of a crude flowing through a pipe, at least one of the wax appearance temperature WAT and the pour point PP of the crude, at least one of the presence of particles and clogging can be determined in step a). Indeed, below the WAT, paraffins may form deposits on the inner walls of the pipeline and lead to pipe clogging, which generates either a high pressure drop or pipe blockage. This paraffinic crude may also gel, in particular during a shutdown phase, and require high pressures to restart. Determining WAT and PP for this type of petroleum fluid is very important to be able to anticipate field architectures and remediation operations.

However, the fluid composition may vary for different reasons (export line carrying a mixture of oils in varying proportions, evolution of the composition of the crude produced during the operating life of the field). This composition variation also induces variations in the WAT and PP values of the transported fluid.

At least one of monitoring and control can be at least one of the following steps:
- optimization of the additives in the fluid, for example anti-freeze additives or pipe unblocker additives;
- monitoring of the appearance of flocculated asphaltenes;
- detection of phenomena related to the instability of products; and
- optimization of the production strategy, for example, within the context of the flow of a crude oil through a pipe, makes possible determination of a maximum allowable shutdown time during which the fluid cools down, or the need to provide heating of the pipe or to determine the frequency of pipe scraping operations.

The method according to the invention enables operators to have access to a real-time WAT and PP measurement, which allows better assessment of the safety margin and thus optimizing their production strategies.

EXAMPLES

The features and advantages of the method according to the invention will be clear from reading the application example hereafter.

In order to illustrate this invention, tests have been carried out on a crude oil by varying the temperature so as to monitor the behavior between wax appearance (WAT) and the curdled state of the system (pour point PP).

A multipoint Sam-Flex™ probe, Indatech-Chauvin Arnoux, was used for the tests. In this example, the measurements were performed with measurement angles of 180°, 175°, 170° and 30° allowing the signal to be measured both in reflection and in transmission as in FIG. 1.

In the configuration used, the air gap of the probe is 3 mm, which is equivalent to the optical path.

The probe was connected to a spectrometer enabling hyperspectral detection for measuring the spectra at the four angles simultaneously (Hy-Ternity™, Indatech-Chauvin Arnoux). The InGaAs sensor provided measurements in the 900-1700 nm spectral range.

The analysed sample was a crude oil whose (initially known) WAT and PP differ by 3° C.

The sample was stirred in a water bath to cover a temperature range from WAT+5° C. to PP−5° C. The spectral measurements were performed both during temperature rise and temperature decrease. The integration time was 6 s every 5 s.

FIG. 2 illustrates signal S (unitless) corresponding to the raw intensity received at the sensor as a function of wavelength L in nm obtained for the 180° measurement angle. Similar curves are obtained for the other measurement angles (not shown). The various curves correspond to the spectra obtained for the different temperatures. The intensity variations observed on the y-axis are caused by the modifications of the analysed medium, themselves due to the change in temperature.

In this curve, the first troughs (around 1200 nm) correspond to the second harmonic of the symmetric and asymmetric stretches of the $CH_2$ and $CH_3$ groups, whereas around 1400 nm, it is the first harmonic of the combination of bands conventionally around 4000 $cm^{-1}$ (combination between the symmetric and asymmetric stretches of the CH bonds in the $CH_2$ and $CH_3$ groups and the deformations of the C-H bonds).

A principal component analysis (PCA) was carried out for multivariate data exploitation. A common component and specific weight analysis (CCSWA) would have been also possible, but here the data was exploited more simply after 2D unfolding.

The objective is to represent, on a limited number of components, most of the SRS information over time. Relevant information could be observed minimum up to the sixth principal component.

The PCA components are orthogonal by construction, that is the information represented on each axis is independent. The scores obtained up to the seventh components are shown in FIG. 3.

FIG. 3 shows the seven principal components C1 to C7 as a function of time T in s. In this figure, the dots correspond to the scores (values for the principal component considered) as a function of time T and the curve corresponds to the temperature of the medium as a function of time T.

Five breaks of slope are observed for these components, two of which correspond to the wax appearance temperature WAT and to the pour point PP of the fluid:
- the WAT is described by the first vertical arrow in dotted line (left) and it is at a first break of slope on components C1, C2, C3 and C5, and
- the PP, described by the second vertical arrow in dotted line, naturally coincides with the expected change in the signal measurement noise: when the product changes from a dynamic circulation mode: rather noisy signal; to a much cleaner signal related to a static mode acquisition, for all of the components.

The other breaks of slope of the components represent other changes in the fluid properties.

Thus, the method according to the invention allows accurate determination of fluid change parameters, such as WAT and PP.

To supplement the previous example, additional tests were carried out and are presented hereafter:

The spectral measurement equipment, probe and spectrometer, and the procedure are the same as in the previous example. However, the temperature cycles range from 40° C. to −20° C. for this example, and this is repeated in order to validate the repeatability of the tests.

For the tests described below, three crudes were used (fractions A, B and C), pure or in admixture, in order to obtain 10 different sample references. The proportions and the WAT values of the sample references are given in the table hereafter:

TABLE 1

| Sample reference | Fraction A | Fraction B | Fraction C | WAT (° C.) |
|---|---|---|---|---|
| 1 | 100% | 0 | 0 | 34 |
| 2 | 0 | 100% | 0 | 20 |
| 3 | 0 | 0 | 100% | 23.4 |
| 4 | 30% | 70% | 0 | 23.8 |
| 5 | 70% | 30% | 0 | 29.2 |
| 6 | 0 | 30% | 70% | 19.6 |
| 7 | 0 | 70% | 30% | 19.7 |
| 8 | 30% | 0 | 70% | 29.5 |

TABLE 1-continued

| Sample reference | Fraction A | Fraction B | Fraction C | WAT (° C.) |
|---|---|---|---|---|
| 9 | 70% | 0 | 30% | 31.8 |
| 10 | 34% | 33% | 33% | 25.8 |

For each sample, the same temperature cycles were applied. The spectra were acquired every minute with an integration time of 90 ms.

To validate the repeatability and the reliability of the tests, the temperature cycle measurements performed on a sample are shown in FIG. 4.

FIG. 4 shows the kinetic traces at 1555 nm for the 4 angles of sample 7 during 4 temperature cycles. There are 4 temperature decreases from 40° C. to −20° C. and 4 temperature rises from −20° C. to 40° C. The figure shows that the intensities I measured at the four angles (30°, 170°, 175°, 180°) as a function of time tin h are very much similar from one cycle to another. Furthermore, FIG. 4 illustrates the curve of temperature T in ° C. as a function of time t in h. This shows the experiments to indeed be repeatable, which validates the operating protocol. Thus, the results can be exploited on a single temperature cycle and they remain valid each time.

As in the previous example, a multivariate data analysis is performed. Thus, a PCA of the spectra of a temperature cycle of all the samples is carried out. The measurements of a temperature cycle of each sample are then alternately projected onto this global PCA for exploitation of the results. This allows tracing for each sample the scores of the first three principal components and to relate each break of slope to the temperature thereof. An example of representation of the scores is shown in FIG. 5 for sample 7.

FIG. 5 shows the scores of the first three principal components (PC1, PC2, PC3) as a function of time tin h during a temperature cycle of sample 7. Furthermore, FIG. 4 illustrates the temperature curve T in ° C. as a function of time t in h. In this figure, vertical lines are added when a change in slope is observed on the scores. This procedure is applied for all the samples. Exploitation of the results shows that the first break of slope is related to the WAT of the samples.

The WAT obtained by studying the scores of the PCA ($T^{ACP}$ in ° C.) was plotted as a function of that measured by use of the reference method (DSC—Differential Scanning calorimetry), WAT in ° C. in FIG. 6, for each sample Ref.1 to Ref.10.

A quasi-linear dispersion of the samples is observed in FIG. 6.

This example, with new crudes, validates the fact that the method according to the invention allows accurate determination of parameters of change in a fluid, such as the WAT.

The invention claimed is:

1. A method of determining at least one parameter representative of a change in a fluid due to a temperature variation of the fluid comprising steps of:
   a) placing the fluid in a medium transparent to radiation in a near-infrared domain;
   b) performing a spectral measurement by use of spatially resolved near-infrared spectroscopy for the fluid placed in the transparent medium, the spectral measurement being performed for at least two measurement angles and for at least two temperatures of the fluid;
   c) performing a multivariate analysis of the spectral measurement as a function of the temperature; and
   d) determining the parameter representative of a change in the fluid by using the multivariate analysis.

2. A method as claimed in claim 1, wherein the parameter representative of a change in the fluid is selected from among wax appearance temperature of the fluid, pour point of the fluid, cloud point, cold filter plugging point, transition threshold between the phases of the fluid, and the parameter is related to an aggregate or an agglomerate of objects within the fluid.

3. A method as claimed in claim 2, wherein the parameter representative of a change in the fluid is the wax appearance temperature of at least one of the fluid and a pour point of the fluid.

4. A method as claimed in claim 1, wherein the fluid is a crude oil.

5. A method as claimed in claim 1, wherein the fluid is placed in a bypass line of a pipe through which the fluid flows.

6. A method as claimed in claim 1, wherein the spatially resolved near-infrared spectroscopy is performed by use of at least one transmission measurement with a measurement angle α ranging between 130° and 180°.

7. A method as claimed in claim 6, wherein the spatially resolved near-infrared spectroscopy is performed by use of at least one reflection measurement ranging between 5° and 90°.

8. A method as claimed in claim 7, wherein the spatially resolved near-infrared spectroscopy is performed by use of at least two transmission measurements with respectively measurement angles selected from between 170°, and 180°, and at least one reflection measurement with a measurement angle.

9. A method as claimed in claim 1, wherein the multivariate analysis is a principal component analysis, a common component analysis or specific weight analysis.

10. A method as claimed in claim 9, wherein the multivariate analysis is performed for at least six components.

11. A method as claimed in claim 9, wherein the parameter representative of a change in the fluid is determined by analysis of at least one of an inflection point, a break of slope and a limitation of noise of at least one component of the multivariate analysis.

12. A method as claimed in claim 1, wherein the spatially resolved near-infrared spectroscopy is carried out with a wavelength variation ranging between 900 nm and 1700 nm.

13. A method as claimed in claim 1, wherein a temperature of the fluid placed in the transparent medium is controlled for carrying out a spectral measurement, by varying temperature of the fluid between a minimum temperature ranging between −20° C. and 15° C. and a maximum temperature ranging between 30° C. and 60° C.

14. A method as claimed in claim 1, wherein the fluid is circulated in a pipe and the spectral measurement is performed in a bypass line of the pipe through which the fluid flows.

15. A method as claimed in claim 14 wherein, during the spectral measurement, circulation of the fluid in the bypass line is stopped.

16. A method of at least one of monitoring and controlling flow of a fluid through a pipe, comprising steps of:
   a) determining at least one parameter representative of a change in the fluid within the pipe due to a temperature variation of the fluid by using the method of claim 1; and
   b) at least one of monitoring and controlling the flow of the fluid through the pipe as a function of the parameter representative of a change determined in the fluid.

17. A method as claimed in claim 2, wherein the parameter is related to an aggregate or an agglomerate of objects within the fluid including one of generation of nano-aggregates, growth of objects or polydispersity of objects.

18. A method as claimed in claim 6, wherein the near-infrared spectroscopy is performed by use of at least one transmission measurement and angle ranging between 130° and 180°.

19. A method as claimed in claim 18, wherein the angle ranges between 165° and 180°.

20. A method in accordance with claim 7, wherein the measurement angle ranges between 5° and 90°.

21. A method in accordance with claim 20, wherein the measurement angle ranges between 20° and 40°.

22. A method in accordance with claim 7, wherein the reflection measurement ranges between 20° and 40°.

* * * * *